United States Patent [19]

Bazzano

[11] Patent Number: 5,183,817

[45] Date of Patent: Feb. 2, 1993

[54] COMBINATIONS OF RETINOIDS AND MINOXIDIL-TYPE COMPOUNDS FOR HAIR GROWTH

[76] Inventor: Gail S. Bazzano, 4506 Avron Blvd., Metairie, La. 70006

[21] Appl. No.: 283,646

[22] Filed: Dec. 13, 1988

Related U.S. Application Data

[63] Continuation-in-part of Ser. No. 136,525, Dec. 22, 1987, abandoned, which is a continuation of Ser. No. 463,146, Feb. 2, 1983, abandoned, which is a continuation-in-part of Ser. No. 235,169, Feb. 17, 1981, abandoned, and a continuation-in-part of Ser. No. 318,607, Nov. 9, 1981, abandoned, and a continuation-in-part of Ser. No. 368,730, Jun. 9, 1982, abandoned, and a continuation-in-part of Ser. No. 414,854, Sep. 3, 1982, abandoned.

[51] Int. Cl.$^5$ .................... A61K 31/505; A61K 31/07
[52] U.S. Cl. .................... 514/256; 514/725; 514/880
[58] Field of Search .................... 514/725, 256, 313

[56] References Cited

U.S. PATENT DOCUMENTS

| | | | |
|---|---|---|---|
| 3,382,248 | 5/1968 | Anthony et al. | 514/880 |
| 3,461,461 | 8/1969 | Anthony et al. | 514/880 |
| 3,464,987 | 9/1969 | Ursprung et al. | 514/880 |
| 3,729,568 | 4/1973 | Kligman | 514/859 |
| 3,882,244 | 5/1975 | Lee | 424/70 UX |
| 3,973,016 | 8/1976 | Morrison | 514/79 |
| 4,139,619 | 12/1979 | Chidsey | 514/725 UX |
| 4,170,229 | 10/1979 | Olson | 424/70 UX |
| 4,220,772 | 9/1980 | Muller et al. | 544/255 |
| 4,232,438 | 3/1982 | Peck | 424/70 UX |
| 4,247,547 | 1/1981 | Marks | 424/70 UX |
| 4,287,338 | 9/1981 | McCall | 544/123 |
| 4,304,787 | 12/1981 | Gander et al. | 424/70 UX |
| 4,333,924 | 6/1982 | Bowley et al. | 424/70 UX |

FOREIGN PATENT DOCUMENTS

| | | | |
|---|---|---|---|
| 158799 | 9/1954 | Australia | 424/70 UX |
| 553262 | 12/1956 | Belgium | 424/70 UX |
| 0242967 | 3/1987 | Fed. Rep. of Germany | 514/859 |
| 51-73137 | 6/1976 | Japan . | |
| 55-9007 | 1/1980 | Japan | 514/313 |
| 906000 | 11/1960 | United Kingdom | 514/859 |
| 1466062 | 2/1977 | United Kingdom | 514/313 |

OTHER PUBLICATIONS

Merck Index 9th edition, 1979, pp. 1060, 1287 to 1289.

*Primary Examiner*—Dale R. Ore
*Attorney, Agent, or Firm*—Panitch Schwarze Jacobs & Nadel

[57] ABSTRACT

Increase in the rate of hair growth, stimulation of hair follicles to produce new hair growth, prolongation of the anagen phase of the hair cycle, conversion of vellus hair to growth as terminal hair, and treatment of alopecias due to organic dysfunction of the hair follicle is attained in mammalian skins by either oral administration or by topical application to the skin, hair and/or hair follicles of the mammal of effective amounts of a retinoid, particularly retinoic acid, and a minoxidil-type compound. The combination may be administered or applied alone or with other adjunctive compounds including vitamins, such as Vitamin $D_3$, hormones, and/or antiandrogens.

30 Claims, No Drawings

COMBINATIONS OF RETINOIDS AND MINOXIDIL-TYPE COMPOUNDS FOR HAIR GROWTH

CROSS-REFERENCE TO RELATED APPLICATIONS

This application is a continuation-in-part of copending application Ser. No. 136,525, filed Dec. 22, 1987, now abandoned, which in turn is a continuation of Ser. No. 463,146, filed Feb. 2, 1983, now abandoned, which in turn is a continuation-in-part of applications Ser. No. 235,169, filed Feb. 17, 1981; Ser. No. 318,607, filed Nov. 9, 1981; Ser. No. 386,730, filed Jun. 9, 1982; and Ser. No. 414,854, filed Sep. 3, 1982, all now abandoned. This application is also related to my co-pending application Ser. No. 283,649, filed concurrently herewith, entitled "Use Of Retinoids And Compositions Containing Same For Hair Growth".

FIELD OF INVENTION

This invention relates to the use of synergistic combinations with minoxidil (2,4,-diamino-6-piperidino-pyrimidine-3-oxide) or certain of its derivatives or analogs in order to increase the rate of and stimulate growth of hair on mammalian skins, particularly human scalp hair to prolong the anagen phase of the hair cycle, to convert vellus hair to growth as terminal hair, and to treat certain types of alopecias.

BACKGROUND OF THE INVENTION

A normal characteristic of hair growth in mammals, including humans, is that in most cases, the rate of hair growth and the length of its growth cycle are reduced with age. Those phenomena are common to all mammals with rare exceptions, and they must be differentiated from true male pattern alopecia, which is caused by target organ sensitivity to androgens.

Several factors may influence the rate of hair growth. These factors include race, sex, age, geography, season of the year, nutrition and hormones. See Myers, R. J. and Hamilton, J. B. "Regeneration and rate of growth of hairs in man" *Ann. N.Y. Acad. Sci.* 53:562-568 (1951); Hamilton, J. B. "Age, sex and genetic factors in the relation of hair growth in man: A comparison of Caucasian and Japanese populations" *The Biology of Hair Growth* (Ed. Montagna, W. and Ellis, R. A.), Academic Press Inc., New York, pp. 400-433 (1958); Yano, S. "Rate of hair growth" *Hifu to Hinyo* 4:546-552 (1936); Maeda, I. "Study on the cuticula of hair: (III) Relation between the cuticula and rate of the growth of human hair" *Jyuzenkai-Zasski*, 43:1298-1304 (1938); Trotter, M. "The resistance of hair to certain supposed growth stimulants" *Arch. Dermatol. and Syphilol.* 7:93-98 (1923); Pinkus, F. "Zur Kenntnis der Lebensdauer der menschlichen terminal haare" *Z. Morphol. und Anthropol.* 24:256-269 (1924); Ono, M. "Studies on the hair growth of beard and scalp hair (1st report) Influencing factor in the rhythms of hair growth" *J. Physiol. Soc. Japan* 25:254-261 (1963).

Various preparations have heretofore been proposed for the treatment of male pattern baldness. It is also a matter of common knowledge, however, that none of the so-called "hair growth formulae" have proven to be very efficacious.

In contrast to most epithelial structures, the hair follicle does not grow continuously throughout its life, but passes through a cycle called the pilar cycle. The pilar cycle comprises essentially three phases—namely, the anagen or growth phase during which hair is produced, normally lasting about three to seven years; the catagen phase when growth stops and the follicle atrophies, lasting about three to four weeks; and the telogen phase, which is a rest period for the follicle during which the hair progressively separates and finally falls out, and normally lasting about three to four months. Normally 80 to 95 percent of the follicles are in the anagen phase, less than 1 percent being in the catagen phase, and the rest being in the telogen phase. Whereas the telogen phase hair is uniform in diameter with a slightly bulbous, non-pigmented root, the anagen phase hair has a large colored bulb at its root.

Alopecia results when the pilar cycle is disturbed, resulting in excessive hair loss. The most frequent phenomenon is a shortening of the hair growth phase due to cessation of cell proliferation. This results in an early onset of the catagen phase, and consequently a large number of hairs in the telogen phase during which the follicles are detached from the dermal papillae, and the hairs fall out. This shortening of the growth or anagen phase of the pilar cycle may have different origins, among which are very diverse pathological origins such as febrile conditions, mental stresses, hormonal problems (such as androgenetic alopecia due to male hormones) and secondary effects of drugs. Alopecia may also be due to age and to a slowing down of mitotic activity. This dysfunction of the biological mechanism of hair growth leading to alopecia may be regarded as a disease. While there are other causes of alopecia such as greasy or oily scalp due to seborrhea and the dandruff accompanying it, the present invention is not directed to treating these extraneous causes of alopecia, but rather to treating the organic dysfunction of the hair follicle.

German Patent No. 2758484 discloses certain chemical preparations for treatment of scalp to prevent baldness. These preparations contain bile compounds as the active ingredients and also include pro Vitamin A or tretinoin. The active ingredient is a product obtained from gall or a derivative thereof such as chenodeoxycholic acid, urodoxy cholic acid and their salts or derivatives.

Another patent is Olsen U.S. Pat. No. 4,140,229 citing the use of Vitamin A-containing crystal clear, transparent, aqueous, sprayable emulsions for reducing itching and flaking of common dandruff and seborrhea. As stated in its abstract, in some instances, the use of such emulsions reduced excessive falling hair. It does not purport to stimulate hair growth. It simply teaches a method of conditioning hair and scalp to effect relief from dandruff symptoms. The only pertinent example in Olson is discussed under Case History No. 3 of Example IV wherein the "Spray-on-Brush-in-Solution" contained Vitamin A palmitate and seven other ingredients. All that is disclosed is that "the daily loss of head hair was reduced to approximately 10 to 20."

Knight British patent specification No. 1,466,062 discloses a cosmetic composition containing tocopherol and retinoic acid as a cosmetic preparation which can be used on the skin or as a hair cleaning or hair dressing agent. This multi-purpose cosmetic composition allegedly prevents age spots, and is claimed to be good for clearing the scalp of dandruff. It appears that, during clearing of the scalp of dandruff with this composition, the scalp can become healthier, hair loss is reduced, and hair growth can recommence. A specific treatment for androgenetic alopecia or male pattern alopecia is not suggested by this disclosure. The use of retinoids to alter the hair follicle growth rate or to prolong the anagen phase of the hair cycle is also not disclosed or discussed by Knight. Knight is claiming a cosmetic lotion for cleaning the scalp. Common dandruff and seborrhea or seborrheic dermatitis (seborrhea is the production of excess sebum and seborrheic dermatitis is an irritation of the scalp), as well as age spots, are the topic of this patent, and the composition used is a combination of two ingredients (Vitamin E and retinoic acid) in a cosmetic base.

There is a reference in the literature to the treatment of monilethrix using tretinoin (retinoic acid). Monilethrix is a vary rare genetic disease in which the hair shaft is defective and the hair is sparse and fragile. Topical application of retinoic acid improved the symptoms of this genetic defect. Hernandez-Perez, E. "Tretinoin therapy for monilethrix" *Archives of Dermatology* 109:575-576 (1974).

The use of retinoic acid in many disease conditions has been recently reviewed in the *Journal of the American Academy of Dermatology* by Haas and Arndt, "Selected therapeutic applications of topical tretinoin" 15:870-877 (1986). The review article in the May 1981 *Journal of the American Academy of Dermatology*, by Thomas, et al. also gives a list of the known uses of retinoic acid, but the treatment of alopecia or androgenetic alopecia is not listed.

There are no references of which I am aware for the use of retinoids in altering the rate of hair growth and treating alopecias, such as androgenetic alopecia. In fact, quite the opposite is the case, and the literature is full of references to hair loss caused by the toxic use of retinoids in high concentrations. References to hair loss caused by retinoids include W. Bollag and A. Matter, "From Vit A to Retinoids in Experimental and Clinical Oncology", p. 9-23, *Modulation of Cellular Interactions by Vitamin A and Derivatives, (Retinoids)* (Eds. Luigi M. DeLuca, Stanley S. Shapiro) Annals of New York Academy of Sciences, Vol. 359 (1981) and *Retinoids: Advances in Basic Research and Therapy* (Eds. C. E. Orfanos) Springer-Verlag (1981)—See articles "Aromatic Retinoids in Psoriasis", p. 165-173, S. Jablouska, et al.; and "Treatment of Severe Forms of Psoriasis and Retinoic Acid Derivatives", J. C. Gatti, et al., p. 185-191.

One compound, minoxidil, a potent anti-hypertensive compound, has been found to promote hair growth when applied topically to the scalp, as discussed in U.S. Pat. No. 4,139,619 and 4,596,812 to Chidsey et al. Minoxidil is recognized as being somewhat effective in producing new vellus hair growth and sparse terminal hair growth in a preselected group of subjects. However, its effect is far from satisfactory in most subjects.

BRIEF SUMMARY OF THE INVENTION

According to the invention it has been found that retinoids or mixtures thereof in combination with minoxidil and/or minoxidil-type compounds are synergistically effective in stimulating or increasing the rate at which hair grows on mammalian skin, prolonging the anagen phase of the hair cycle, converting vellus hair to terminal hair growth, and treating alopecias due to organic dysfunction of the hair follicle by topical application to the hair and hair follicles and to the skin adjacent thereto. Preparations such as lotions, creams, shampoos, and the like, containing the aforementioned compounds as the active ingredients, can be applied topically to the skin, hair and/or follicles for this purpose. Oral administration of the retinoids may also be used. Other adjunctive compounds which may be included in the compositions of the invention include vitamins, such as Vitamin $D_3$, hormones, and antiandrogens. The invention also includes the topical or oral administration of retinoids to fur bearing animals or birds to increase the rate of hair growth and/or retard shedding or molting.

DETAILED DESCRIPTION OF PREFERRED EMBODIMENTS

Retinoids have been shown to cause elevated DNA synthesis in keratinocytes in cell culture. Retinoids can also be shown to increase the turn-over time of epidermal cells in cell culture experiments as well as in vivo experiments with human subjects. As disclosed in my copending application Ser. No. 283,649, the present inventor has discovered that the cells of the hair follicle, particularly the keratinocytes, can be stimulated by retinoids. When tested experimentally, the retinoids caused the cells of the dermal papillae and the keratinocytes, as well as cells of the root sheath, to incorporate more tritiated thymidine into DNA and to reproduce at a more rapid rate than untreated cells from other hair follicles. This stimulation by the retinoid compounds ultimately causes the entire hair follicle to become more activated and the mitotic index, as measured by thymidine-$H^3$ incorporation into DNA, to rise. Therefore, the individual scalp hairs can be shown to grow at an increased rate, and the anagen phase is prolonged.

A major problem in influencing alopecia is to revascularize the area of alopecia and initiate the primary new hair growth. Retinoic acid and its derivatives and the other retinoid compounds have been shown to give excellent percutaneous absoprtion and to be very active on the keratinizing cells of the skin, including the hair follicle. However, it is difficult for retinoids alone to revascularize the area of the pilosebaceous apparatus.

Studies have shown that minoxidil, a potent antihypertensive medication and peripheral vasodilator, can increase the rate of hair growth on the body when taken systemically, particularly in areas of the limbs and facial areas, possibly due to vasodilatory properties. Further studies have suggested that minoxidil may be effective in initiating and promoting vellus hair growth on the scalp of individuals with alopecia. However, minoxidil may not able to sustain the growth of terminal hairs from vellus hairs on the scalp. In the majority of subjects with alopecia, terminal hair growth on the scalp may not be initiated or sustained by the topical application of minoxidil nor by its systemic administration.

Minoxidil has been shown to prolong the life of keratinocytes in culture and extend the time after confluence that cells can be subcultured. These data suggest that the mechanism by which minoxidil exerts its effect is that the drug reduces the rate at which cells are lost from the germinative pool and hence slows senescence. See J. Kubilus et al., "Effect of Minoxidil on Pre- and Postconfluent Keratinocytes," *Journal of the American Academy of Dermatology*, 16:648 (1987). Vascular effects alone do not appear to be a sufficient stimulus for hair growth, particularly in an area affected by alopecia. As described in my copending application Ser. No. 283,649, the disclosure of which is incorporated herein by reference, retinoids can stimulate and increase the rate of hair growth in both males and females and can prolong the anagen phase of the hair cycle, as well as converting vellus to terminal follicles. The mechanism of action of the retinoid compounds is believed to be through the initiation and activation of increased cell turnover and cell differentiation, i.e., compounds which of themselves can initiate the differentiation of cells of the pilosebaceous apparatus which eventually form the hair follicle and become terminal hairs.

Because of the advanced state of scalp thinning and atrophy of the pilary portion of the pilosebaceous apparatus, it is difficult to initiate hair growth from areas of advanced male pattern alopecia. Retinoid compounds sustain and promote hair growth in areas where hair is present to some extent.

The present invention combines the use of retinoid compounds with minoxidil, or its analogs or derivatives or minoxidil-type compounds (hereinafter collectively referred to simply as "minoxidil"). The stimulatory actions of both compounds can synergistically promote each others' effect. Retinoids can initiate cell growth and differentiation (not initiated by minoxidil), and minoxidil can promote the vasodilatory and mitogenic action not obtained with the retinoids. While neither compound alone may have profound effects on advanced alopecias, in combination the compounds are very effective as promoters of new hair growth in areas of alopecia.

The net result of application of minoxidil and retinoids is initiation and production of new hair growth and conversion of vellus to terminal hair growth, i.e., the increase in size from a vellus to a terminal hair and the continued and more prolonged maintenance of the hair in the anagen phase. As noted previously, this effect is obtained not merely as the addition of two compounds, but as synergism, i.e., the combination of these substances in the present invention produces an effect which cannot be produced by either compound separately under conditions of its use and, therefore, represents a major advance in the treatment of alopecia.

Suitable retinoid active ingredients for use in this invention include derivatives of retinoic acid (Vitamin A acid or tretinoin) which may be represented by the following formulae:

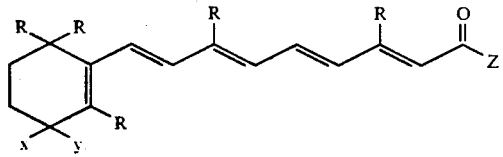

wherein R is hydrogen or a lower alkyl group, X is individually hydrogen and Y is individually hydrogen or a hydroxy group, or X and Y together form oxo, and Z is alkoxy, amide, alkylamide, hydroxy, nitro, or other suitable terminal groups. Also included by the above formula are pharmaceutically accepted salts thereof.

Further, the basic formula may include the dehydro, dihydro, or anhydro forms, such as the 7,8-dehydro and 5,6-dihydro forms, of retinoic acid as well as all of the stereoisomeric forms thereof, such as the 9-cis; 9,13-dicis; 13-cis; 11-cis; 11,13-dicis; etc. Examples are shown as follows:

13-cis-retinoic acid

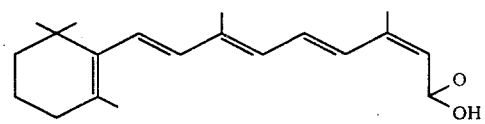

9-cis-retinoic acid

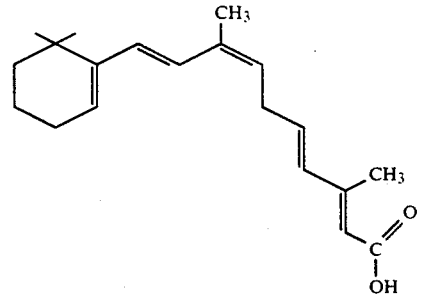

7,8-dehydro-retinoic acid

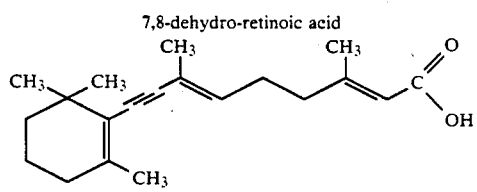

5,6-dihydro-retinoic acid

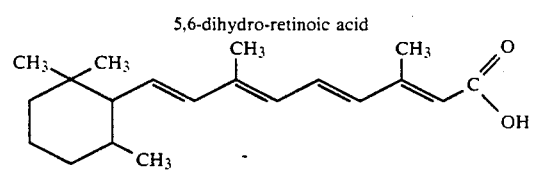

The anhydro forms may be represented by the following compounds:

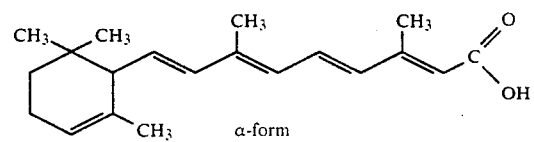

α-form

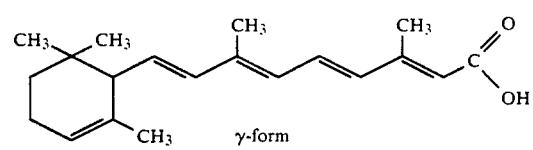

γ-form

Suitable retinoid analogs and derivatives useful in the invention have the following general formulae wherein the side chain, the ring, or both, may be altered:

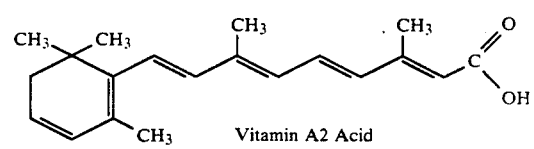

Vitamin A2 Acid

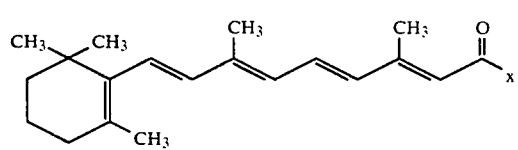

wherein X is a member selected from the group consisting of: —OHCH₂CONH₂; mixed —OCH₂CH(OH)CH₃ and —OCH(CH₃)CH₂OH; —OCH ; as well as

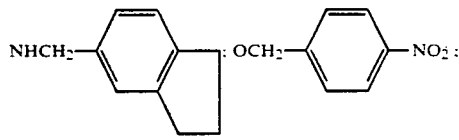

—OCH₂—C₆H₅; and —OCH₂CO—

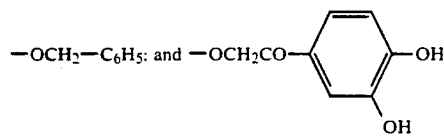

These compounds as well as other alkoxy and amide compounds can be active as they can be hydrolyzed to retinoic acid and other active compounds in the body. However, their activity may not be as direct as all-trans retinoic acid.

Other suitable retinoid compounds useful in the invention include α-hydroxy retinoic acid represented by the formula:

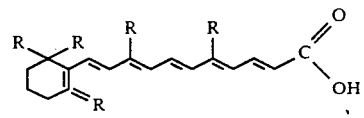

and the C₂₂-analog of retinoic acid represented by the following general formula:

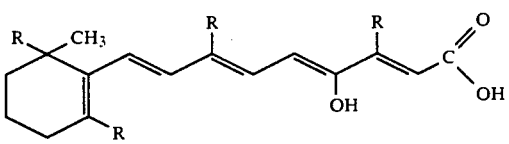

wherein R in both of the above formulae are lower alkyl radicals, preferably methyl groups.

Other structurally modified retinoids which, to some degree, exhibit the activity of retinoic acid for hair growth purposes can be presented by the following general formulae:

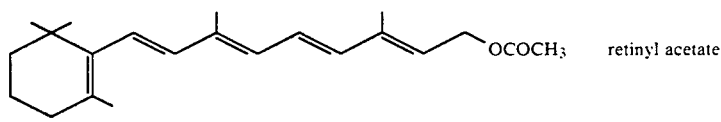
retinyl acetate

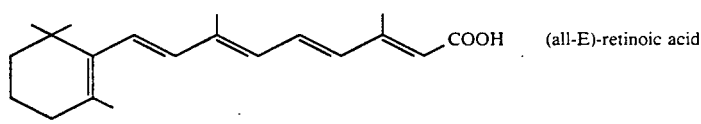
(all-E)-retinoic acid

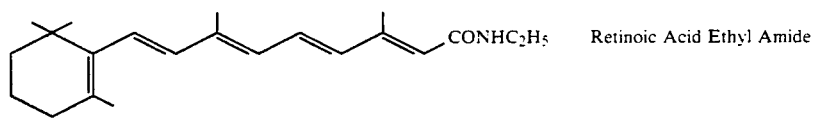
Retinoic Acid Ethyl Amide

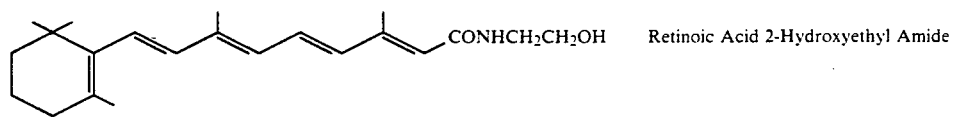
Retinoic Acid 2-Hydroxyethyl Amide

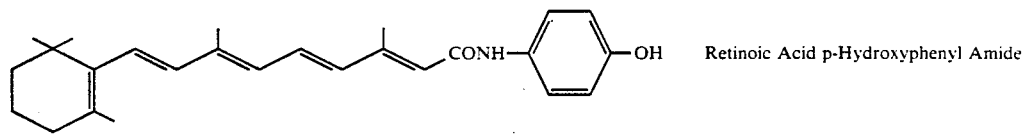
Retinoic Acid p-Hydroxyphenyl Amide

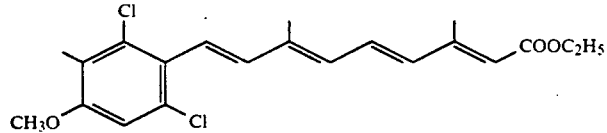

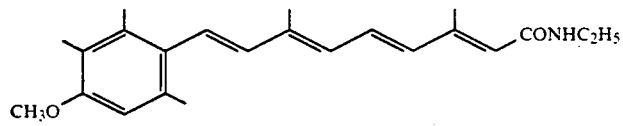

-continued
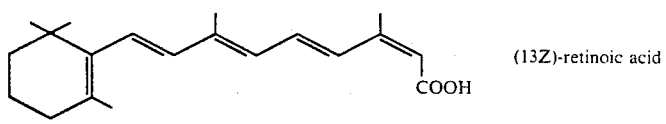 (13Z)-retinoic acid
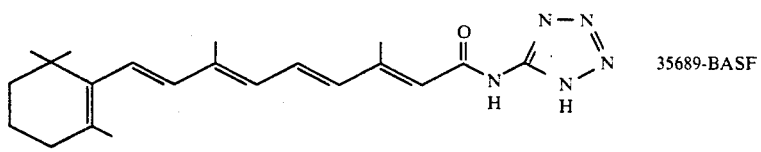 35689-BASF
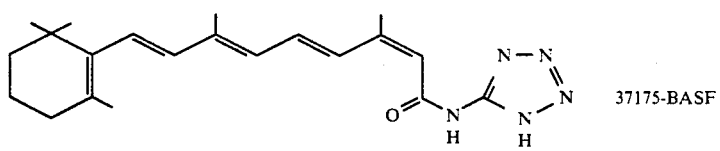 37175-BASF
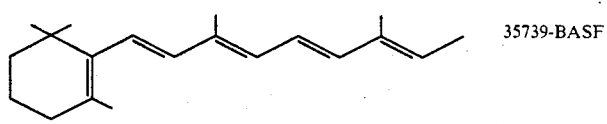 35739-BASF
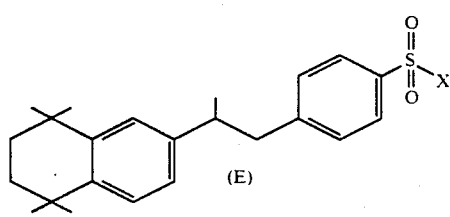 (E)
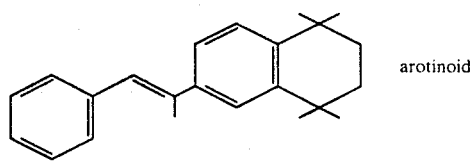 arotinoid
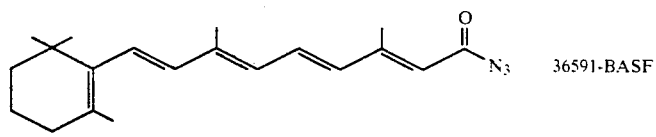 36591-BASF
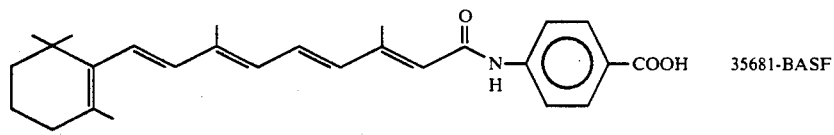 35681-BASF
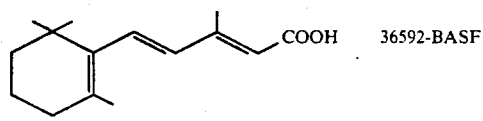 36592-BASF
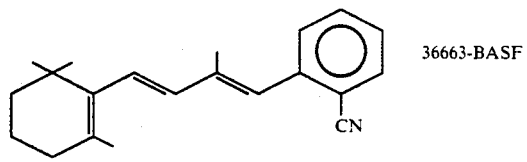 36663-BASF -continued

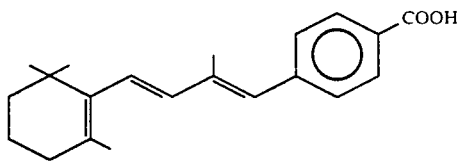 37400-BASF

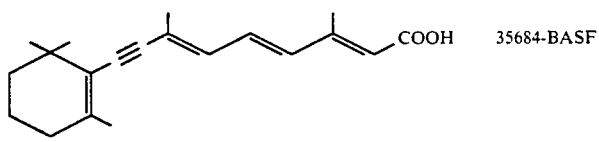 35684-BASF

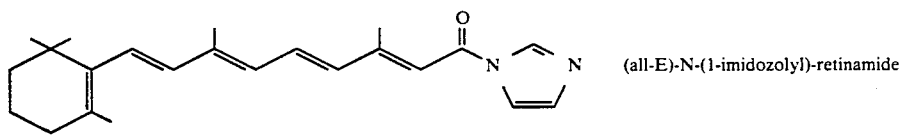 (all-E)-N-(1-imidozolyl)-retinamide

Still other useful analogs and derivatives of retinoic acid and retinoids include the following compounds:

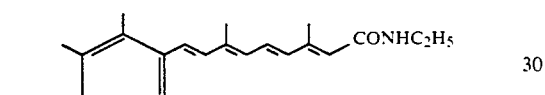

Trimethylmethoxphyenyl (TMMP) analog of retinoic acid ethylamide (Motretin)

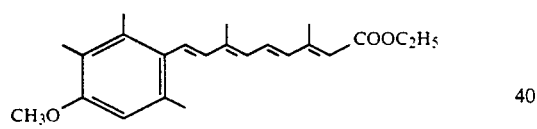

Trimethyimelhoxphenyl (TMMP) analog of retinoic acid ethyl ester (Etretinate)

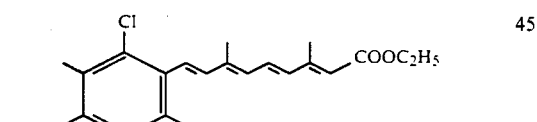

Dichloromethylmethoxphenyl (DCMMP) analog of retinoic acid ethylester

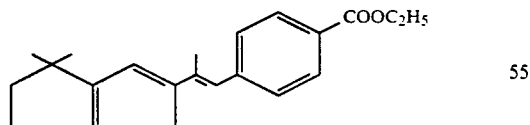

Arotinoid ethyl ester

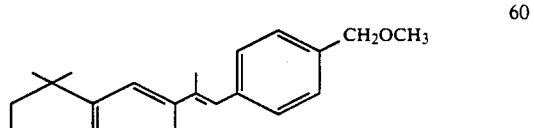

Arotinoid

-continued

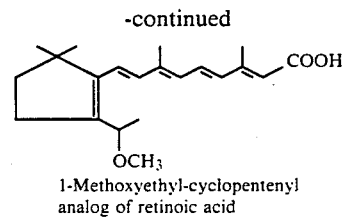

1-Methoxyethyl-cyclopentenyl analog of retinoic acid

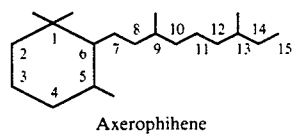

Axerophihene

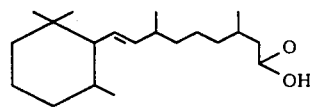

13-cis-Retinoic acid

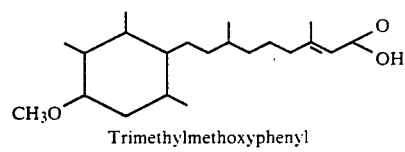

Trimethylmethoxyphenyl

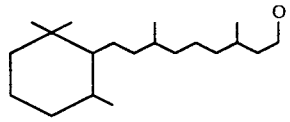

Retinal

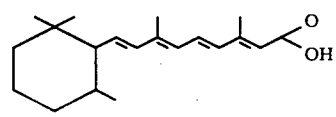

β-all-trans-Retinoic acid (RA)

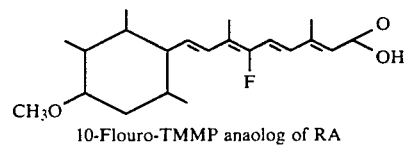

10-Flouro-TMMP anaolog of RA

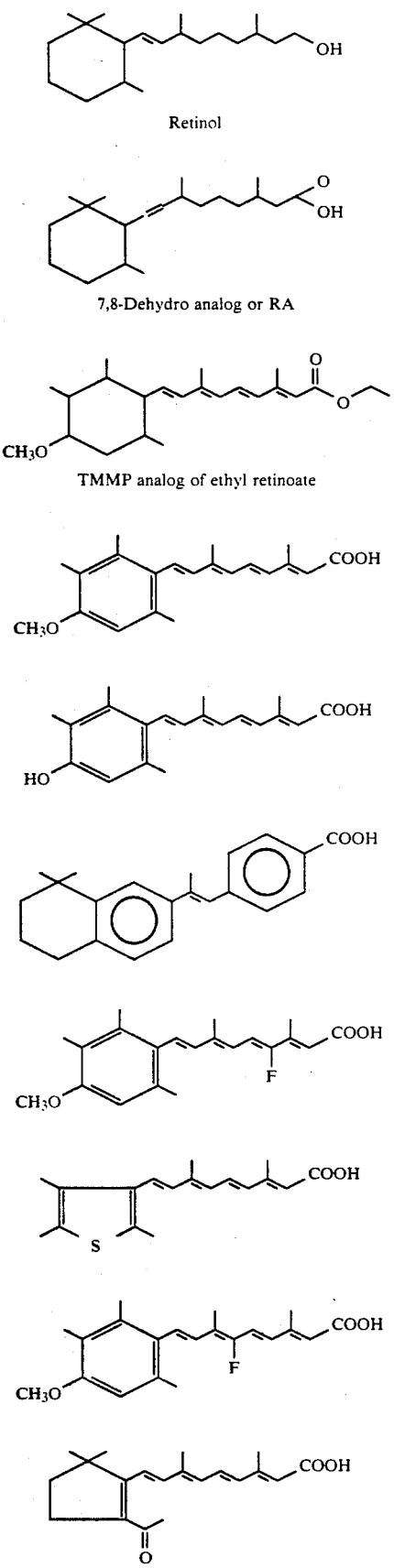
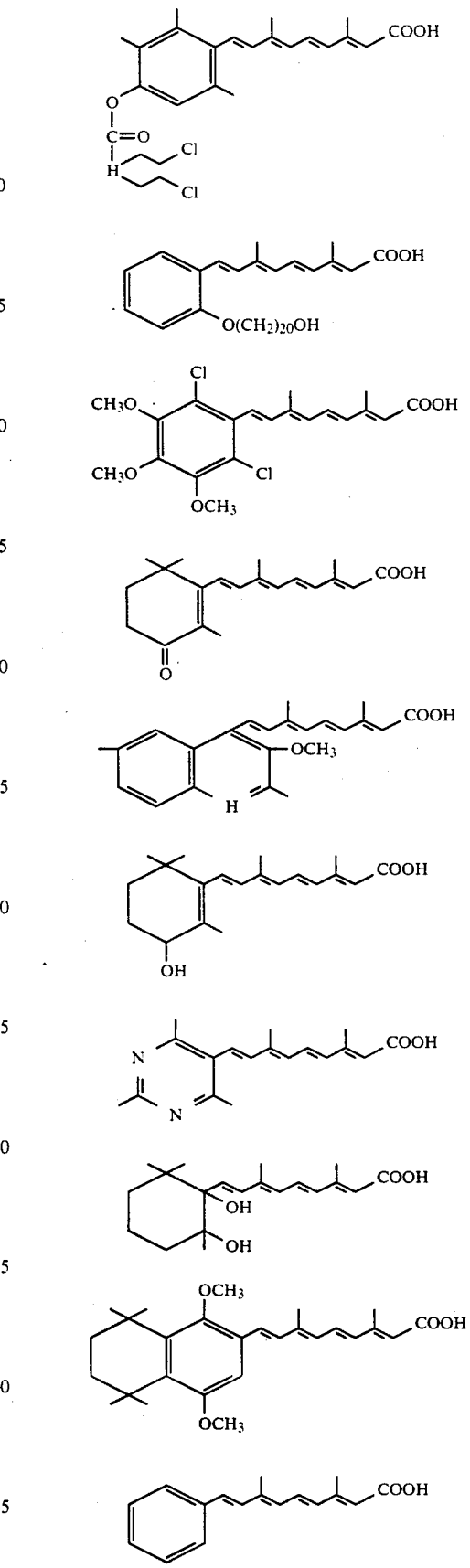

-continued
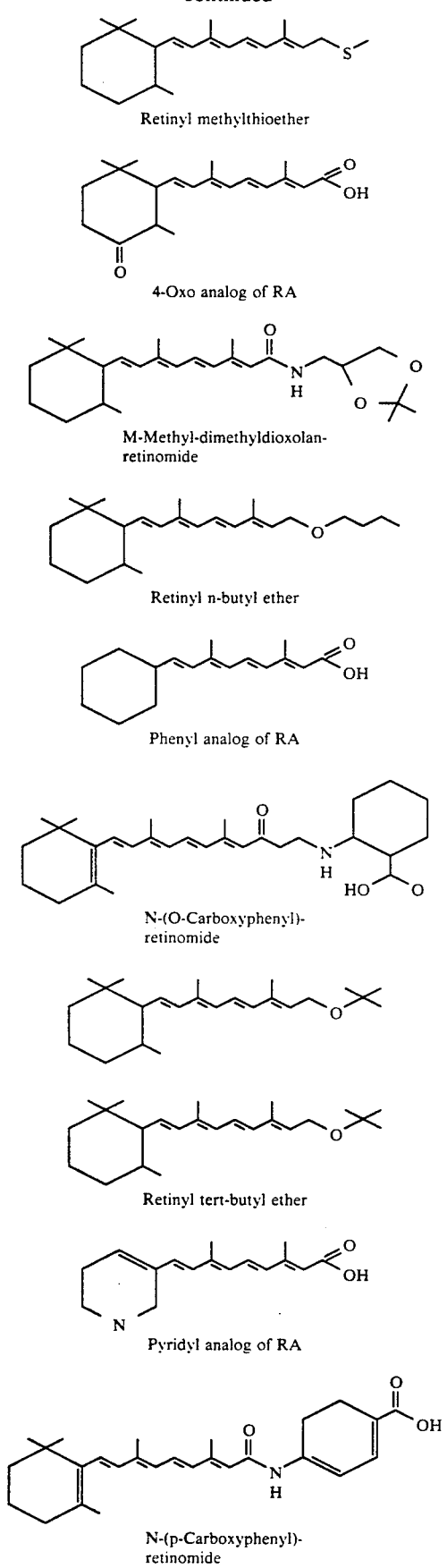
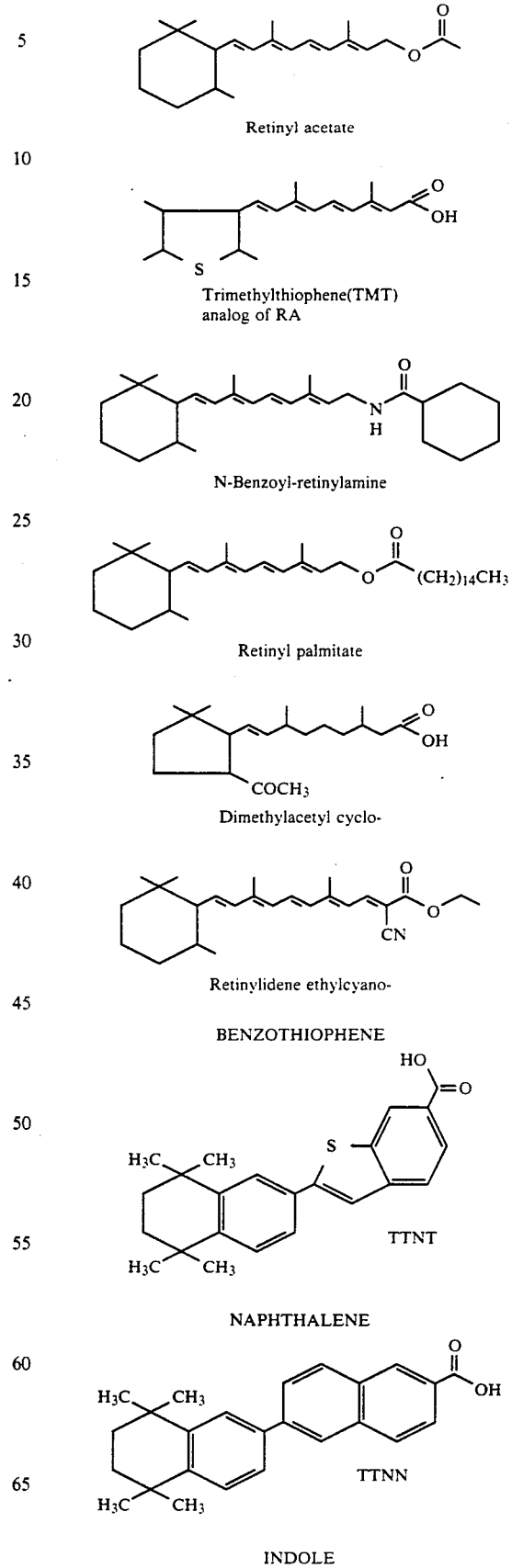

-continued

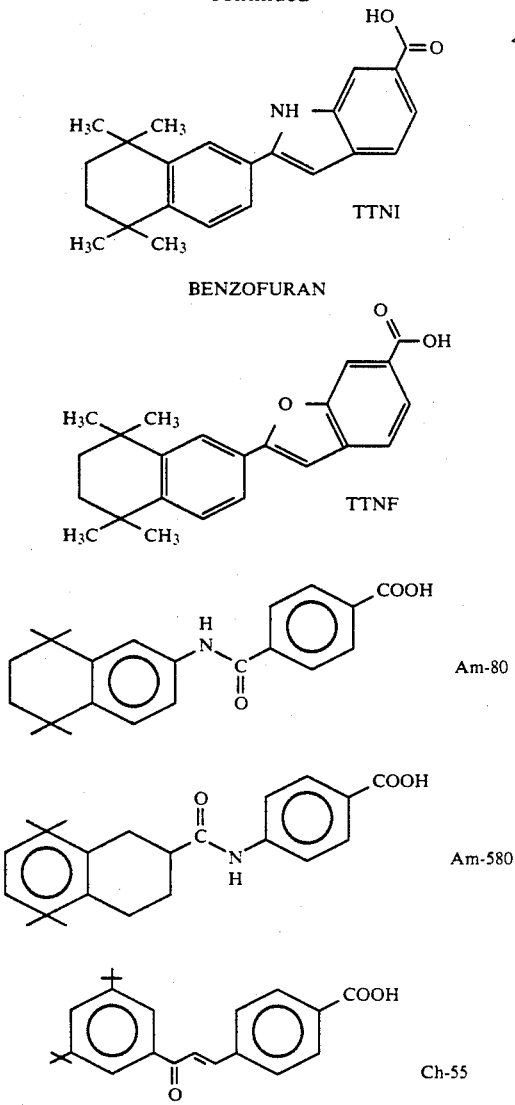

Also included within the foregoing compounds are any halogenated compounds or ether, amide, modified rings, dehydro, dihydro, isomer or analog forms of said compounds.

The retinoid compounds useful in the present invention are believed to have the common characteristic of binding to the retinoid cell receptors and thereby stimulating the hair follicle cell proliferation.

Retinoids have been defined narrowly as comprising simply Vitamin A (retinol) and its derivatives such as Vitamin A aldehyde (retinal), Vitamin A acid (retinoic acid), comprising the so-called natural retinoids. Retinol and its esters have been used previously in hair preparations to prevent hair loss, but not to increase or stimulate hair growth in cases of alopecias.

Subsequent research has resulted in a much larger class of chemical compounds that are termed retinoids due to their biological similarity to Vitamin A and its derivatives. Compounds useful in the present invention include natural forms of Vitamin A, Vitamin A acid and its isomers, Vitamin A aldehyde and/or synthetic analogs of Vitamin A acid which possess the biological activity of Vitamin A acid in the hair follicle. Accordingly, as used herein for purposes of the present invention, the term "retinoid" will be understood to include any compound which fits the foregoing chemical and/or biological definitions.

That is, the definition of a retinoid intended in this invention is a substance that can elicit a specific biological response by binding to and activating a specific receptor or set of receptors for retinoids. Therefore, any Vitamin A type compound, whether defined by the classic description of a particular subset of diterpenoid, polyene substances or a new type of synthetic ligand (neither diterpenoid nor polyene) which can have a better molecular fit to the retinoid receptors (cytosolic retinoic acid binding proteins), should be considered in this definition. The biological response of the target cells for retinoids should be defined as any compound (retinoid) which is capable of stimulating the hair follicle cells to differentiate or to turnover more rapidly. This covers compounds traditionally related to retinoids and it also covers compounds which are not diterpenoid types. The ring, the side chain, the terminal group or all of these can be altered. This definition would include even newer retinoids which do not fit the older Vitamin A-type concept but which can be shown to bind to the retinoid receptor proteins specific for retinoic acid (CRABP) within cells of the follicular epithelium. Examples of such newer retinoids include, inter alia, TTNT, TTNN, TTNI, TTNF, Am-80, Am-580 and Ch-55, which are shown above.

Minoxidil (2,4-diamino-6-piperidinopyrimidine-3-oxide) is represented by the following formula:

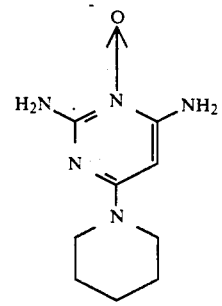

In addition to minoxidil, its active derivatives and analogs can also be used. These active derivatives and analogs are described, for example, in U.S. Pat. Nos. 5,910,928; 3,637,697; 3,461,461; 4,139,619; and 4,596,812, the descriptions of which are fully incorporated herein by reference.

Among the active derivatives and analogs of minoxidil described in these patents are compounds of the formula:

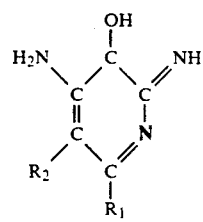

where $R_1$ is a moiety selected from the group consisting of moieties of the formula

wherein $R_3$ and $R_4$ are selected from the group consisting of hydrogen, lower alkyl, lower alkenyl, lower arylalkyl, and lower cycloalkyl, and taken together $R_3$ and $R_4$ may be a heterocyclic moiety selected from the group consisting of aziridinyl, acetidinyl, pyrrolidinyl, piperidino, hexahydroazepinyl, heptamethylenimino, octamethylenimino, morpholino, and 4-lower alkylpiperazinyl, each of said heterocyclic moieties having attached as substituents on the carbon atoms 0-3 lower alkyl groups, hydroxy or akloxy, and wherein $R_2$ is selected from the group consisting of hydrogen, lower alkyl, lower alkenyl, lower alkoxyalkyl, lower cycloalkyl, lower aryl, lower aralkyl, lower alkaryl, lower alkaralkyl, lower alkoxyaralkyl, and lower haloaralkyl, and the pharmacologically acceptable acid addition salts thereof.

See also *J. Heterocyclic Chem.*, 15:1529 (1978) by John M. McCall, et al., the disclosure of which is additionally incorporated herein by reference.

Included as minoxidil analogs are those described in the following U.S. Pat. Nos.: 4,287,338; 4,220,772; 3,464,987; 4,316,901; 3,270,015; 3,270,014; 3,382,248; 3,461,461; 4,080,500; and 3,973,016, the disclosures of which are incorporated herein by reference. Other suitable minoxidil-type compounds include minoxidil glucuronides disclosed in published European application 0242967A1 and the substituted pyrimidine compounds disclosed in my published PCT patent applications WO86/00616 and WO/8504577.

A major problem in influencing hair growth is obtaining good percutaneous absorption of the active compounds. The retinoid compounds described herein cause excellent percutaneous absorption of themselves and other compounds used in combination therewith, and are very active on the keratinizing cells of the skin, including the hair follicles.

Accurate measurement of hair growth to substantiate the results of the testing is often a problem. A microcapillary method which gives excellent results and can be used to measure the rate of hair growth was devised by M. Saitoh, et al., *Advances in Biology of the Skin*, vol. 6, p. 467 (1968) and utilizes microcapillary tubes which are graduated using 0.2 mm graduations. A less time-consuming magnification method which also yields good results involves shaving off of the hairs for examination and measurement.

The pharmaceutical, cosmetic or veterinary preparations of the present invention can be prepared by conventional techniques for the preparation of lotions, creams, conditioners or shampoos for the scalp or veterinary preparations for pelts. Though not as preferred, included also are preparations which can be administered orally and compounds which can be added to animal foods.

In addition to the active combinations of retinoids and minoxidil-type compounds of this invention, the various preparations can contain any conventional pharmaceutically acceptable or cosmetically acceptable inert or pharmacodynamically active additives or carriers. For example, the lotions may be prepared using various forms of alcohols or other solubilizers such as glycols or esters. The conditioners may contain the normally acceptable, commercially produced compounds such as cetyl alcohol, cetearth-5, -20 hydantoins, hydrolyzed animal protein, glycol stearate, amodimethicone, paraffin, mineral oil, silicones, etc.

The topical compounds may also contain various adjunctive compounds, such as oils, including essential fatty acids; vitamins or their derivatives; hormones (natural or synthetic), including progesterones, estrogens including estradiols, thyroids, and polypeptide hormones; and antiandrogens, including but not limited to cyproterone acetate, cyoctol, secosteroids, flutamide or spironolactone, and particularly nonsteroidal antiandrogens such as the decahydro-7H-benz(E)-inden-7-ones described in U.S. Pat. No. 4,466,971. Androgens are known to cause alopecia in genetically programmed individuals, and antiandrogens prevent the effect of the androgen on the nucleus of the hair follicle cell. Therefore, any substance which can prevent the androgen from acting on the nucleus of the cell is considered an antiandrogen.

Examples of the active-type Vitamin $D_3$ which can be used in combination with the retinoids of this invention include the following types which are not meant to be limiting: 1-hydroxycholecalciferol; 1,25-dihydroxycholecalciferol (commercially available as ROCALTROL); and 1,24-dihydroxycholecalciferol. Vitamin D3 is generally administered at a rate of about 0.001 to 0.3 $\mu$g/gm. Vitamin $D_3$ type compounds have recently been shown to regulate cell differentiation and to promote the differentiation of the keratinocyte. Vitamin D compounds are also important in calcium regulation. These compounds may assist in the conversion of vellus to terminal hairs.

The topically applied lotions, creams, conditioners, or other formulations containing the retinoid will vary according to the standard art with regard to the amounts of other hydrophilic and hydrophobic ingredients, including emulsifiers, so that either an oily, semi-oily or oil-free product may be obtained. The shampoos may contain any of the conventionally used detergents or soaps and any other compounds used by those familiar with the art. Oil-based shampoos are included in these formulations.

The oral preparations may be tablets, liquids, capsules, etc. The pharmaceutically acceptable substances commonly used as preservatives, stabilizers, moisture retainers, emulsifiers, etc., can be present in these preparations. Conventionally acceptable antioxidants such as tocopherols, N-methyl 2-tocopheramine, butylated hydroxyanisole (BHA) and butylated hydroxytoluene (BHT), can be incorporated also in the preparations described herein.

Retinoids and minoxidil are administered in effective amounts which vary with the route of administration and the requirements of the subjects. The topical treatments may consist of lotions, creams, conditioners, shampoos, oil treatments, etc., with about 0.001 to 2% by weight of all-trans retinoic acid or derivatives, or other retinoids, as the preferred dosages in the described compositions and with dosages of about 0.01% to 30% minoxidil in suitable vehicles for topical use. Arotinoids may be effectively used at doses as low as 0.00001% by weight or even lower. Oral dosages for minoxidil should not exceed 10 mg/day total dose, and for retinoic acid 1 mg/kg body weight/day is a maximal dose which will eventually cause toxicity and with chronic treatment will probably cause the hair to fall out. Therefore, 0.1 mg/kg body weight should be a median or acceptable dose.

In order to examine the specific action of the retinoids and minoxidil in increasing the rate of hair growth, several types of experiments were performed. The microcapillary method was used in each case to measure the rate of hair growth. Other methods of dye staining and hair growth measurements were also undertaken. In addition, the method of Ebling, et al., *Journal of Investigative Dermatology*, November 1981, was used to study the conversion of vellus to terminal hairs by microscopy.

The effectiveness of the active ingredients of this invention for increasing the rate of or stimulating hair growth will now be illustrated by the following examples. These examples, however, are merely representative and should not be construed so as to limit the scope of the invention.

EXAMPLE I

A topical lotion containing 0.1 percent by weight of all-trans retinoic acid and 3% by weight minoxidil was included in the preparation to be tested. As the vehicle, 5 weight percent propylene glycol, 1 mg per 100 ml butylated hydroxytoluene (BHT), and 95 weight percent ethanol were mixed in a beaker for several minutes at ambient conditions to obtain a homogeneous preparation in which the retinoid was dissolved. This lotion was labelled A and was the active drug preparation. A similar lotion was prepared by the foregoing procedure containing all the aforementioned ingredients, but omitting the retinoid and minoxidil. This preparation was labelled B and was the placebo lotion.

Volunteer subjects had a 3 to 4 cm diameter area of scalp hair bleached at the scalp end. The subjects were asked to apply the (placebo) lotion B, 2 times a day, to the scalp for varying periods of time from 10 to 30 days. The rate of hair growth in each individual was determined using measurements taken with either microcapillary measuring equipment or by magnification measurements. The rate of new hair growth from the scalp end to the bleached area was recorded every three to six days. The data is expressed as control rate of hair growth in mm of growth per day.

At the end of the placebo treatment, anagen/telogen ratios were determined by the following standard method of Orentreich, N. and Berger, R. A. "Selenium disulfide shampoo", *Arch. Derm.* 90:76-80 (1964): Hair plucking was done from the areas treated before and after treatment. A large surgical-needle-holding clamp, with jaws covered with a smooth layer of rubber was used. Twenty to fifty hairs were grasped at one time, approximately 1.0 cm above the scalp surface, and epilated with a single forceful pull. The hair roots and lower portion of the shafts were then cut off into shallow plastic Petri dishes, previously gridded into 1 cm squares, moistened with tap water, and examined and counted by transmitted light with a low-power dissecting microscope. The roots could also be stained to help in the interpretation.

Following the placebo treatment, the subjects were given lotion A (containing the active drug) or lotion B and asked to apply the lotion in the same manner in which they had applied the previous (placebo) lotion. The same procedure was followed for measuring hair growth, namely every three to six days the subject returned for measurements to determine rate of hair growth. At the end of the active drug treatment period, subjects again had anagen/telogen ratios determined. Neither the subjects nor the observers were told which lotion A or B was the active preparation until after the data were analyzed.

Before treatment and at monthly intervals thereafter, a circle 1 inch in diameter was drawn over the balding spot of the vertex with a skin marker and a template. The center of the circle was located by a three-point measurement, using the midpoint between the ears and a fixed distance from the base of the nose. These measurements were recorded at each visit. With the aid of a magnifying lens, the hairs in the 1-inch diameter circle were counted and typed as vellus hairs, indeterminate hairs, or terminal hairs. Nonpigmented short hairs were defined as vellus; pigmented hairs ranging from thin and short to slightly longer and thicker were defined as indeterminate. Hairs of the same color and bore diameter as those in adjacent nonbalding areas were classified as terminal. The count was repeated several times and the average used as the final count. The number of vellus and terminal hairs were compared before, during and at the final visit, and calculated as percent conversions from vellus to terminal.

In Table I are described the results of studies using male and female subjects. The all-trans retinoic acid and minoxidil in lotion form was applied topically or as described in Table I, and hair growth rates were assessed along with conversion of vellus to terminal hair.

TABLE I

| | | | | | Lotion Containing All-Trans Retinoic Acid 0.1% and Minoxidil 3% | | |
|---|---|---|---|---|---|---|---|
| Subject | | Dosage | Form of | Treatment Time | Rate of Growth (mm/day) | | % Conversion Vellus to |
| Sex | Age | (ml/day) | Dosage | (Months) | Control (Lotion B) | Treatment (Lotion A) | Terminal |
| M | 37 | 10 | Topical | 2 | 0.23 | 0.30 | 11% |
| M | 62 | 10 | Topical | 2 | 0.21 | 0.29 | 22% |
| M | 38 | 10 | Topical | 2 | 0.35 | 0.42 | 35% |
| F | 43 | 10 | Topical | 2 | 0.37 | 0.39 | 13% |
| F | 38 | 10 | Topical | 2 | 0.31 | 0.35 | 18% |
| F | 64 | 10 | Topical | 2 | 0.24 | 0.29 | 17% |

COMPARATIVE STUDY

A group of twenty normotensive subjects, twenty to sixty-four years of age and clinically diagnosed as suffering from androgenetic alopecia, were entered into a combined study in which twelve subjects received 0.025% topical tretinoin solution with the vehicle as discussed above (95% ethanol, 5% propylene glycol and 1 mg BHT per 100 ml), 36 subjects received a combination of 0.025% tretinoin and 0.5% minoxidil solution, five subjects received the vehicle alone as a placebo, three subjects received 0.5% minoxidil solution alone, according to the following protocol. Food coloring was added to the placebo and minoxidil solutions to match the color of the retinoic acid.

The subjects were instructed to apply 1 ml of the solution twice daily by dropper to the affected scalp area (a circular area of baldness, 1 inch in diameter). The subjects were advised to wear a cap for protection from the sun or to refrain from excessive sun exposure, and to avoid trauma to the scalp (i.e., vigorous scalp scrubbing or brushing). Blood pressure, serum chemistry tests, complete blood counts, weight, pulse and electrocardiogram were performed before treatment and at repeated intervals for each patient; skin irritation was assessed during each follow-up visit; photographs were taken before and during treatment to evaluate hair growth; and hair counts were performed initially, at monthly intervals, or at follow-up visits.

After analysis of the data, the subjects were placed into one of three designated response groups, with percent increase in number of terminal hairs (defined as thick, pigmented hairs, comparable to those on the subjects' posterior scalp) being the primary criterion for placement. Participants in the "good" response group (Group A) experienced greater than 46% increase in the number of hairs in the target area after treatment; individuals in the "moderate" response group (Group B) had a post-therapy terminal hair increase between 21% and 45%; while participants in the "no response" group (Group C) experienced increases below 20%. The mean amount of time for subject participation was 10, 8 and 9 months, respectively, for Groups A, B and C, and the results are indicated in Table II below.

TABLE II

| Treatment | No. of Patients | Response Good (Group A) | Moderate (Group B) | None (Group C) |
| --- | --- | --- | --- | --- |
| Placebo | 5 | 0 | 0 | 5 (100%) |
| Minoxidil | 3 | 0 | 0 | 3 (100%) |
| Tretinoin | 12 | 2 (16%) | 5 (42%) | 5 (42%) |
| Combination | 36 | 16 (44%) | 8 (22%) | 12 (33%) |

In 56 subjects, 48 of whom were receiving tretinoin or the combination formulation, positive responses were documented in more than half of the subjects, usually within 18 months. The five patients receiving placebo demonstrated no significant hair growth response. Three patients receiving the 0.5% minoxidil solution also showed no meaningful results. Of the 5 men who received tretinoin only, two experienced some hair growth after treatment, although the hairs were mostly of the lanugo (vellus) type.

However, surprisingly, of the patients treated with the combination solution (0.5% minoxidil and 0.025% tretinoin), 66% responded positively, with 44% placed in the good response group and 22% in the moderate response group. These data suggest that there may be a synergism between minoxidil and tretinoin when the substances are combined and used topically. While neither compound alone appears to have profound effects on advanced alopecias, in combination the compounds may be more effective as promoters of new hair growth in individuals with alopecia.

While this study used only 0.5% minoxidil in combination with retinoic acid, other studies report that 2% to 5% minoxidil concentrations cause a cosmetically visible hair regrowth in 30% to 40% of subjects. The above results show that low concentrations of minoxidil (only 1/4 to 1/10 the topical minoxidil concentrations previously reported) are effective when used in combination with tretinoin, suggesting that mixtures of minoxidil and retinoids may be more effective in the treatment of alopecia than is minoxidil alone.

More details of the above study, including photographs of the patients, may be found in Bazzano et al., "Topical Tretinoin for Hair Growth Promotion," *Journal of the American Academy of Dermatology*, 15:4, Pages 880–883 and 889–893 (October 1986).

The following Examples illustrate forms of topical application of compositions of the present invention. The methods of administration may vary by lotion, cream, ointment, pill, supplement to animal food, coating for seeds, etc. These Examples are only meant to be illustrative, and do not limit the mode of administration nor the ingredients which can be admixed to the present invention, nor the amounts which may be used.

FORMULATION EXAMPLE I

Lotion Formulation for the Topical Administration

| Ingredients | Weight % |
| --- | --- |
| All-trans retinoic acid or 13-cis retinoic acid | 0.01 to 0.1 |
| Minoxidil | 0.5 to 5.0 |
| Ethanol | q.s. to 100.0 |
| Propylene glycol | 5.0 to 50.0 |
| Butylated hydroxytoluene (BHT) | 0.1 |
| Distilled water | up to 10.0 |

FORMULATION EXAMPLE II

Cream Conditioner for Topical Administration

| Ingredients | Weight % |
| --- | --- |
| All-trans retinoic acid or 13-cis retinoic acid | 1.0 |
| Minoxidil | 10.0 |
| Distilled water | q.s. to 100.0 |
| Cetrimonium Chloride | 5.0 |
| Cetyl alcohol | 4.0 |
| Ethanol | 4.0 |
| Butylated hydroxytoluene | 1.0 |
| Hydrolized animal protein | 0.5 |
| Methylparaben, propylparaben | 0.1 |
| Stabilizer | 0.1 |

In this example, a higher concentration of active ingredient was used since the conditioner is rinsed out shortly after application.

FORMULATION EXAMPLE III

Hydrophilic Ointment for Topical Administration

All-trans retinoic acid (0.01 to 0.1 gram) and 1-10 grams of minoxidil are dissolved in 100 ml of acetone, and the solution is then admixed with 900 g of USP grade hydrophilic ointment to a uniform consistency; one gram of butylated hydroxytoluene is added. A water washable cream ointment is thus prepared.

FORMULATION EXAMPLE IV

Tablets for Oral Administration

| Ingredients | Amounts |
| --- | --- |
| Minoxidil | 10 mg. |
| All-trans retinoic acid or | 25 mg. |

| Ingredients | Amounts |
| --- | --- |
| 13-cis retinoic acid | |
| Lactose | 52 mg. |
| Cornstarch | 20 mg. |
| Microcystalline cellulose | 40 mg. |
| Talc | 2.5 mg. |
| Magnesium stearate | 0.5 mg. |

The active ingredients are mixed with lactose and granulated using a cornstarch paste. The remainder of the above adjuvants are then admixed therein, and the mass is tableted. The tablets are then coated with a water-soluble or water-swellable lacquer. Liquids, syrups or other formulations can be made consistent with pharmaceutical art.

The retinoid/minoxidil combinations of the invention may also be used in veterinary preparations or feeds to increase the rate of growth of fur (pelt) in certain fur bearing animals and to retard shedding and molting.

In fur bearing animals, the rate of fur growth, length of hair, thickness of hair and molting season are controlled by many factors including season, light (wavelength) periodicity, temperature, hormonal factors and nutrition. Controlling all of these variables is impossible. However, animals were selected and areas over the hind quarters were shaved in 2 inch diameter circular areas. In some of the animals the areas were treated topically with all-trans retinoic acid, and in other animals the retinoid was administered orally in animal chow. Some of the animals served as their own controls, using treated and non-treated areas.

In fur bearing animals, the guard hairs and the pile hairs differ in thickness, length and growth rate. In the rabbits studied, the guard hairs averaged 34 mm and the pile hairs 30 mm in length. The effect of topical application of all-trans retinoic acid was to increase the rate of new hair growth. An effect on the non-shaved fur bearing areas treated with topical all-trans retinoic acid in lotion form, was a decrease in the shedding or molting of fur. The mean rate of hair (fur) growth from treated shaved areas was 0.3 mm per day for 3 rabbits (mean) while in non-treatment shaved areas it averaged 0.2 mm per day (mean of 3 rabbits).

The effect could also be demonstrated in domestic cats and dogs; the same type of experimental procedures were used. The most striking effect in long haired dogs and cats was the retardation of molting or hair shedding. Long haired dogs and cats tended to retain more hair in the anagen phase and there was approximately 50% less shedding during the treatment periods. Both methods of administration were satisfactory. Either topical lotion or cream treatment or systemic treatment by inclusion in animal chow was satisfactory. The daily dosage for animals was 20 mg per kilogram animal chow or 10 to 15 mg applied topically.

Commerically important fur bearing animals were also used for experimentation. Two male minks were closely clipped over the back hind quarters. The animals were treated on one hind quarter and the other was used as the control. The microcapillary method for measuring hair growth was used for these studies. The animals were treated by two different methods. The animals were either fed the retinoid in their chow or they were administered the retinoid topically. The daily dose was 20 mg per kg animal chow or 5 mg per day applied topically. The results of these experiments showed that the rate of growth of new pelt was increased approximately 30% by the retinoid treatment.

Experiments using birds (canaries and parakeets) showed that inclusion of the all-trans retinoic acid or the ethyl ester of all-trans retinoic acid in bird food at a dosage of 30 mg per kilogram bird seed retarded the molting process.

The present invention may be embodied in other specific forms without departing from the spirit or the central attributes thereof and, accordingly, reference should be made to the appended claims, rather than to the foregoing specification as indicating the scope of the invention.

I claim:

1. A composition for treating alopecia comprising a retinoid and a minoxidil compound, said compound being present in an amount of about 0.01 to 30 percent by weight and said retinoid being present in an amount of about 0.001 to 2 percent by weight in said composition.

2. A composition according to claim 1 wherein said retinoid is Vitamin A acid.

3. A composition according to claim 1 wherein said compound is minoxidil (2,4-diamino-6-piperidino-pyrimidine-3-oxide).

4. A composition according to claim 3 wherein said retinoid is Vitamin A acid.

5. A composition according to claim 1 wherein said composition also includes a pharmaceutically effective vehicle for said compound and said retinoid.

6. A composition according to claim 5 wherein said vehicle comprises ethanol and propylene glycol.

7. A composition according to claim 1 wherein said compound has the formula:

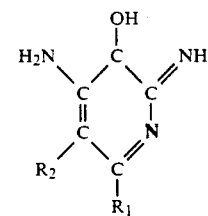

wherein $R_1$ is a moiety selected from the group consisting of moieties of the formula

wherein $R_3$ and $R_4$ are selected from the group consisting of hydrogen, lower alkyl, lower alkenyl, lower aralkyl, and lower cycloalkyl, and taken together $R_3$ and $R_4$, may be a heterocyclic moiety selected from the group consisting of aziridinyl, azetidinyl, pyrrolidinyl, piperidino, hexahydroazepinyl, heptamethylenimino, octamethylenimino, morpholino, and 4-lower alkyl-piperazinyl, each of said heterocyclic moieties having attached as substituents on the carbon atoms 0-3 lower alkyl groups, hydroxy or alkoxy, and wherein $R_2$ is selected from the group consisting of hydrogen, lower alkyl, lower alkenyl, lower alkoxyalkyl, lower cycloalkyl, lower aryl, lower aralkyl, lower alkaryl, lower alkaralkyl, lower alkoxyaralkyl, and lower haloaralkyl, and the pharmacologically acceptable acid addition salts thereof, said retinoid and said compound being applied in amounts which are effective to increase the rate of hair growth.

8. A composition for treating topically alopecia in a pharmaceutically-acceptable vehicle for topical application comprising minoxidil in an amount of about 0.01 to 30 percent by weight and all-trans retinoic acid in an amount of about 0.001 to 2 percent by weight.

9. In a composition for treating alopecia comprising in a pharmaceutically-acceptable vehicle for topical application a compound of formula:

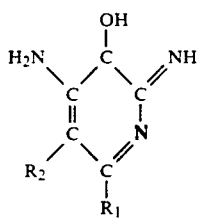

where $R_1$ is a moiety selected from the group consisting of moieties of the formula

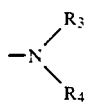

wherein $R_3$ and $R_4$ are selected from the group consisting of hydrogen, lower alkyl, lower alkenyl, lower aralkyl, and lower cycloalkyl, and taken together $R_3$ and $R_4$, may be a heterocyclic moiety selected from the group consisting of aziridinyl, azetidinyl, pyrrolidinyl, piperidino, hexahydroazepinyl, heptamethylenimino, octamethylenimino, morpholino, and 4-lower alkylpiperazinyl, each of said heterocyclic moieties having attached as substituents on the carbon atoms 0-3 lower alkyl groups, hydroxy or alkoxy, and wherein $R_2$ is selected from the group consisting of hydrogen, lower alkyl, lower alkenyl, lower alkoxyalkyl, lower cycloalkyl, lower aryl, lower aralkyl, lower alkaryl, lower alkaralkyl, lower alkoxyaralkyl, and lower haloaralkyl, and the pharmacologically acceptable acid addition salts thereof, the improvement consisting of said composition containing a retinoid in an amount of about 0.001 to 2 percent by weight to increase the rate of hair growth.

10. In a method for treating alopecia caused by a shortening of the anagen phase of the hair cycle, which comprises applying to the scalp an effective amount of a compound of the formula:

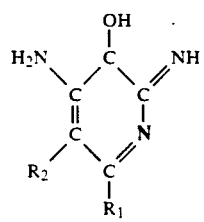

wherein $R_1$ is a moiety selected from the group consisting of moieties of the formula

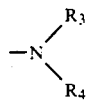

wherein $R_3$ and $R_4$ are selected from the group consisting of hydrogen, lower alkyl, lower alkenyl, lower aralkyl, and lower cycloalkyl, and taken together $R_3$ and $R_4$, may be a heterocyclic moiety selected from the group consisting of aziridinyl, azetidinyl, pyrrolidinyl, piperidino, hexahydroazepinyl, heptamethylenimino, octamethylenimino, morpholino, and 4-lower alkylpiperazinyl, each of said heterocyclic moieties having attached as substituents on the carbon atoms 0-3 lower alkyl groups, hydroxy or alkoxy, and wherein $R_2$ is selected from the group consisting of hydrogen, lower alkyl, lower alkenyl, lower alkoxyalkyl, lower cycloalkyl, lower aryl, lower aralkyl, lower alkaryl, lower alkaralkyl, lower alkoxyaralkyl, and lower haloaralkyl, and the pharmacologically acceptable acid addition salts thereof, the improvement consisting of said topical application including a retinoid in an amount which is effective to increase the rate of hair growth.

11. In a method for treating alopecia caused by a shortening of the anagen phase of the hair cycle which comprises topically applying to the scalp an effective amount of minoxidil, the improvement consisting of said topical application including all-trans retinoic acid in an amount of 0.001 to 2 percent by weight.

12. A method for treating alopecia caused by a shortening of the anagen (growing) phase of the hair cycle, which comprises topically applying to the scalp a retinoid and a compound of the formula:

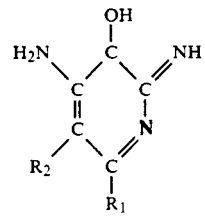

wherein $R_1$ is a moiety selected from the group consisting of moieties of the formula

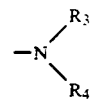

wherein $R_3$ and $R_4$ are selected from the group consisting of hydrogen, lower alkyl, lower alkenyl, lower aralkyl, and lower cycloalkyl, and taken together $R_3$ and $R_4$, may be a heterocyclic moiety selected from the group consisting of aziridinyl, azetidinyl, pyrrolidinyl, piperidino, hexahydroazepinyl, heptamethylenimino, octamethylenimino, morpholino, and 4-lower alkylpiperazinyl, each of said heterocyclic moieties having attached as substituents on the carbon atoms 0-3 lower alkyl groups, hydroxy or alkoxy, and wherein $R_2$ is selected from the group consisting of hydrogen, lower alkyl, lower alkenyl, lower alkoxyalkyl, lower cycloalkyl, lower aryl, lower aralkyl, lower alkaryl, lower alkaralkyl, lower alkoxyaralkyl, and lower haloaralkyl, and the pharmacologically acceptable acid addition salts thereof, said retinoid and said compound being applied in amounts which are effective to increase the rate of hair growth.

13. A method for treating alopecia caused by a shortening of the anagen (growing) phase of the hair cycle, which comprises topically applying to the scalp a minoxidil compound and a retinoid, said compound and said retinoid being applied in amounts which are effective to stimulate hair follicles of said scalp to produce hair growth therefrom.

14. A method for treating alopecia caused by a shortening of the anagen (growing) phase of the hair cycle, which comprises topically applying to the scalp a minoxidil compound and a retinoid, said compound and said retinoid being applied in amounts which are effective to prolong the anagen phase of the hair cycle.

15. A method for treating alopecia caused by a shortening of the anagen (growing) phase of the hair cycle, which comprises topically applying to the scalp a minoxidil compound and a retinoid, said compound and said retinoid being applied in amounts which are effective to convert vellus hair to growth as terminal hair.

16. A method of retarding shedding in fur bearing animals comprising topical administration to the animal of an effective amount of a retinoid and a minoxidil compound.

17. A method of retarding molting in birds comprising topical administration to the bird of an effective amount of a retinoid and a minoxidil compound.

18. In a method for treating alopecia caused by a shortening of the anagen (growing) phase of the hair cycle which comprises topically applying to the scalp an effective amount of a minoxidil compound, the improvement consisting of said topical application including a retinoid in an amount which is effective to increase the rate of hair growth.

19. A method for treating alopecia caused by a shortening of the anagen (growing) phase of the hair cycle, which comprises topically applying to the scalp a minoxidil compound and a retinoid, said compound and said retinoid being applied in amounts which are effective to increase the rate of hair growth.

20. A method according to claim 19 wherein said retinoid is Vitamin A acid.

21. A method according to claim 19 wherein said compound is minoxidil (2,4-diamino-6-piperidino-pyrimidine-3-oxide).

22. A method according to claim 21 wherein said retinoid is Vitamin A acid.

23. A method according to claim 19 wherein said compound and said retinoid are applied in combination with a pharmaceutically acceptable vehicle.

24. A method according to claim 23 wherein said vehicle comprises a mixture of ethanol and propylene glycol.

25. The method of claim 19 wherein said retinoid is selected from the group consisting of all-trans retinoic acid, all-trans retinaldehyde, all-trans retinoyl acetate, and pharmaceutically acceptable salts, ethers, amides or esters thereof.

26. The method of claim 19 wherein the retinoid is an isomer of Vitamin A acid selected from the group consisting of 13-cis; 9,13-dicis; 9-cis; 11-cis; or 7,8-dehydro retinoic acid; Vitamin $A_2$ acid; $\alpha$-Vitamin A acid; $\gamma$-Vitamin A acid; 5,6-epoxy Vitamin A acid; dehydrovitamin A acid; anhydro Vitamin A acid; and pharmaceutically acceptable salts of said isomer.

27. The method of claim 23 wherein said combination further comprises Vitamin $D_3$ or a Vitamin $D_3$ derivative selected from the group consisting of 1-hydroxycholecalciferol; 1,25-dihydroxycholecalciferol; and 1,24-dihydroxycholecalciferol.

28. The method of claim 23 wherein said combination further comprises a hormone selected from the group consisting of estrogens and progesterones.

29. The method of claim 23 wherein said combination further comprises an antiandrogen selected from the group consisting of cyproterone acetate, spironolactone, secosteroids, flutamides, cyoctol, and decahydro-7H-benz(E)-inden-7-ones.

30. A method for treating alopecia caused by a shortening of the anagen phase of the hair cycle which comprises topically applying to the scalp minoxidil and all-trans retinoic acid in amounts which are effective to increase the rate of hair growth.

* * * * *